United States Patent

Kobayashi et al.

[11] Patent Number: 5,993,000
[45] Date of Patent: Nov. 30, 1999

[54] DISPLAY DEVICE

[75] Inventors: Yasushi Kobayashi, Moriguchi; Kenji Ishibashi, Izumi, both of Japan

[73] Assignee: Minolta Co., Ltd., Osaka, Japan

[21] Appl. No.: 09/120,188

[22] Filed: Jul. 22, 1998

[30] Foreign Application Priority Data

Jul. 28, 1997 [JP] Japan ................................ 9-201381

[51] Int. Cl.[6] .................................................. A61B 3/10
[52] U.S. Cl. ........................................................ 351/211
[58] Field of Search .................................. 351/204, 205, 351/211, 212, 206, 246, 247

[56] References Cited

U.S. PATENT DOCUMENTS 4,420,228  12/1983  Humphrey ........................ 351/212
5,355,181  10/1994  Ashizaki et al. .
5,790,235   8/1998  Kirschbaum ...................... 351/246

Primary Examiner—George Manuel
Attorney, Agent, or Firm—Burns, Doane, Swecker & Mathis, LLP

[57] ABSTRACT

A display device provides a virtual image for eyes of an observer. The display has a light source which emits light based on an image signal, scanner which scans the light, an eyepiece optical system which projects the scanned light onto an eye of the observer as a virtual image, detector which detects a pupil size of the observer, and regulator means which regulates a quantity of light projected onto the eye of the observer based on the detected pupil size.

18 Claims, 8 Drawing Sheets

DISPLAY DEVICE

RELATED APPLICATIONS

This application is based on application No. 9-201381 filed in Japan, the content of which is hereby incorporated by reference.

BACKGROUND OF THE INVENTION

1. Field of the Invention

The present invention relates to a display device which presents the eye of an observer with a virtual image of an image photographed by a video camera, computer graphic or other such electronic image.

2. Description of the Related Art

In order to achieve light weight and compactness in a display device which projects an image onto the eye of an observer as a virtual image, the use of a two-dimensional viewing means structured as compactly as possible is desired. Two-dimensional display means include a display which displays a two-dimensional image directly (e.g., which effects display by illuminating a two-dimensional liquid crystal display controlled on the basis of an image signal), and a scanning-type display which displays a two-dimensional image by using a scanner to scan light emitted from a point light source.

In order to make such display device compact, it is advantageous to make the incident light beam diameter presented to the observer as small as possible. Particularly in a device employing a scanning-type display means, the smaller the incident light beam diameter presented to the observer is made, the more lightweight and compact a rotating reflecting mirror or other such scanner can be made. Faster scanning is thereby afforded, a device can be made more lightweight and compact, and highly detailed image display can also be effected.

If the diameter of the incident light beam is made smaller than the pupil diameter of the observer, the amount of light reaching the retina of the observer does not change even if the pupil diameter of the observer changes. The image presented to the observer will consequently be an unnatural one differing from a realistic image, the reason being that the mechanism controlling the human pupil is extremely sensitive to changes in external brightness and reacts to external dynamic changes in brightness by changing the pupil diameter to regulate the amount of light reaching the retina.

For example, when a highly brilliant image meets the eye, its dazzling quality causes the pupil of an observer to contract, but when the diameter of the incident light beam is made smaller than the pupil diameter of the observer, the amount of light reaching the retina of the observer is not reduced, and the observer feels that the viewed image continues to change, becoming brighter. Conversely, even when an image changes to one of low brightness, the observer will be similarly presented with an unnatural sensation without purpose.

Under such conditions which differ from realistic conditions, wherein change in the pupil diameter of an observer does not function adequately to regulate the quantity of light, the visual function or nerve function of an observer may also be damaged. As the foregoing description provides, reducing the light beam diameter presented to the eye of an observer engenders a number of disadvantages. Yet there is no prior art which solves these several problems.

SUMMARY OF THE INVENTION

An object of the present invention is to resolve the aforementioned disadvantages.

A further object of the present invention is to provide a display device which is lightweight and compact and presents a natural image to an observer.

A further object of the present invention is to provide a display device which is highly minute and presents a natural image to an observer.

A still further object of the present invention is to provide a display device wherein quantitative light regulation is accomplished by changes in the pupil diameter of an observer.

An even further object of the present invention is to provide a display device which is lightweight and compact and affords highly detailed image display and which ensures safety for the visual function and nerve function of an observer.

These and other objects are attained by a display device provided with a projector which projects an image onto the eye of an observer as a virtual image, a pupil diameter detector which detects the pupil diameter of an observer, and a luminance regulator which regulates the amount of light presented to an eye according to the results of detection by a pupil diameter detector.

The aforementioned objects of the present invention are also attained by a display device provided with a light source which emits light based on an image signal, a scanner which scans light emitted from a light source, an eyepiece optical system which projects scanned light onto the eye of an observer as a virtual image, a detector which detects the pupil size of an observer, and a regulator which regulates the quantity of light projected onto the eye of an observer according to a detected pupil size.

The invention itself, together with further objects and attendant advantages, will be best understood by reference to the following detailed description taken in conjunction with the accompanying drawings.

BRIEF DESCRIPTION OF THE DRAWINGS

In the following description, like parts are designated by like reference numbers throughout the several drawings.

DESCRIPTION OF THE PREFERRED EMBODIMENTS

Preferred embodiments of the present invention are described hereinafter with reference to the accompanying drawings. Preferred embodiments 1 through 3 represent the present invention applied in a head-mounted display which uses a two-dimensional display element and an illuminating light source as a two-dimensional display means. Preferred embodiments 4 through 6 represent the present invention applied in a head-mounted display which uses a point light source and a two-dimensional scanning means as a two-dimensional display means.

First Embodiment

Figure 1:
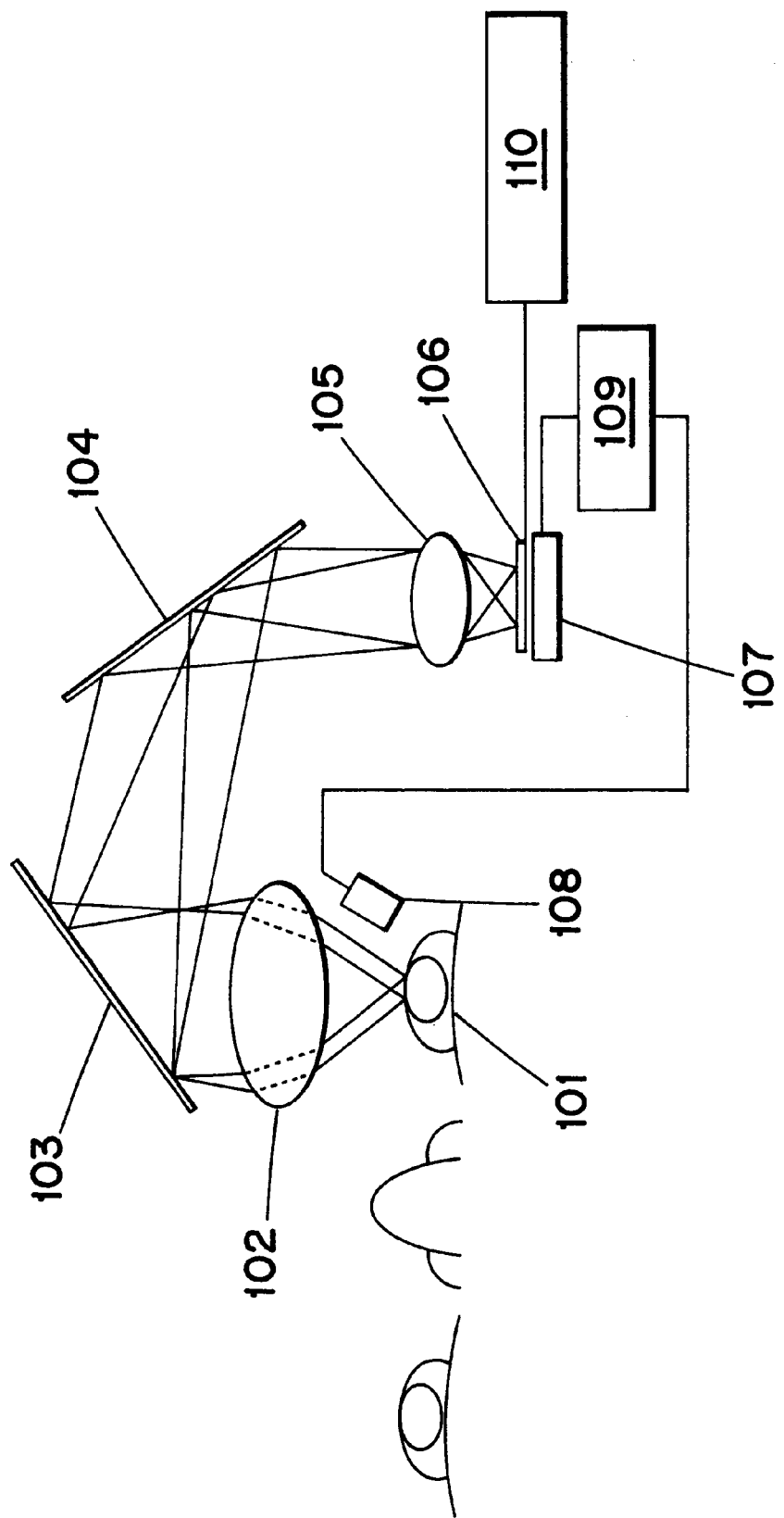
FIG. 1 is a conceptual schematic drawing of a head-mounted display pertaining to a first preferred embodiment.

FIG. 1 illustrates a conceptual schematic drawing of a head-mounted display pertaining to the present preferred embodiment. Numbered element 110 is an image generator. Numbered element 106 is a transmitting-type two-dimensional display element driven by image generator 110. Numbered element 107 is a backlight which illuminates two-dimensional display element 106 from the rear surface. Numbered element 105 is a relay optical system which forms an intermediate image of the light beam emitted from two-dimensional display element 106. A virtual image of the aforementioned intermediate image travels via eyepiece optical system 102 and is projected onto observer eye 101. A light beam passing through relay optical system 105 is reflected by mirrors 104 and 103 and presented to observer eye 101.

Relay optical system 105 is constructed at the near conjugate position to the pupil of observer eye 101. In other words, the smaller the light beam of incident light presented to observer eye 101 is made, the more compactly relay optical system 105 can be structured.

Numbered element 108 is a video camera used to detect pupil diameter. Pupil diameter is calculated based on the result of photography and then output. Numbered element 109 is a regulator which regulates luminance. Luminance regulator 109 regulates the amount of light presented to observer eye 101 by controlling the intensity of backlight 107 according to a detection signal from video camera 108. In the case of a device in which an observer views an image with both eyes, a structure like that in FIG. 1 may be disposed symmetrically about a left-right axis. If there is no great difference in an image presented to both a left and a right eye, it is acceptable to detect the pupil diameter of only the left or the right eye of the observer. In other words, it is acceptable to furnish a mechanism for detecting pupil diameter (video camera 108 or luminance regulator 109) to one eye alone.

A reflecting-type two-dimensional display element may be used rather than the aforementioned two-dimensional display element 106, and a structure providing illumination from its front surface is also acceptable. In this instance too, as above, the quantity of illuminating light is regulated by luminance regulator 109. An EL or other such luminescent two-dimensional display element may also be used rather than a display means comprising two-dimensional display element 106 and backlight 107. In this instance, the display element itself is the light source, and it is therefore acceptable that luminance regulator 109 regulate luminance by controlling a drive device for the luminescent two-dimensional display element.

Figure 2:
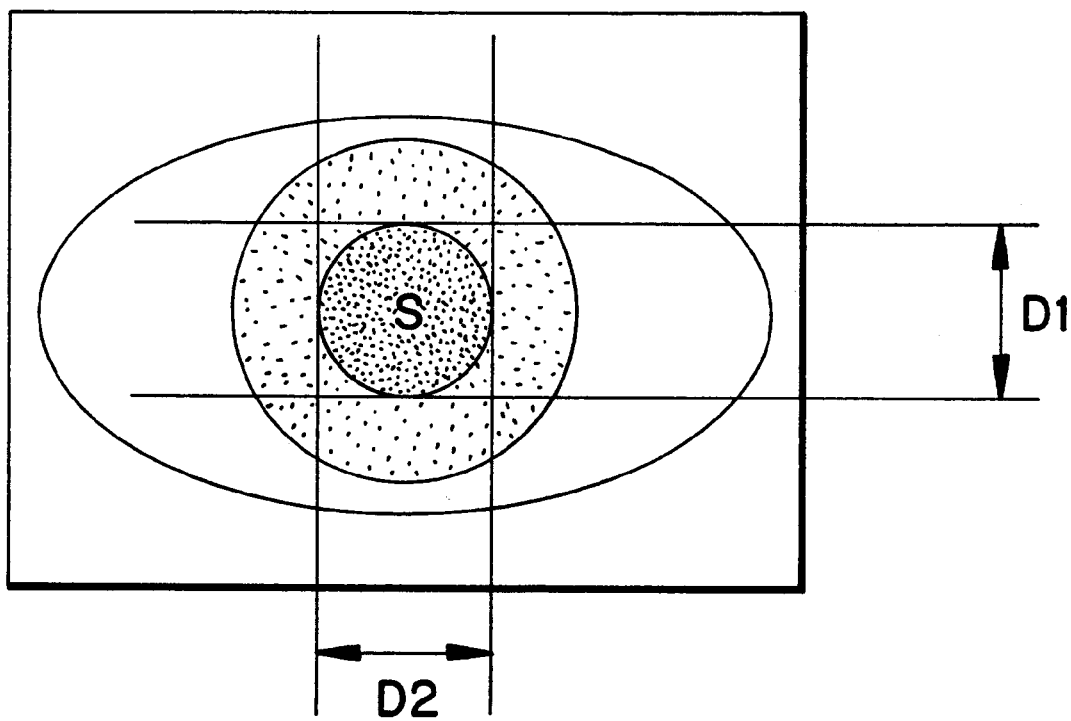
FIG. 2 is a drawing illustrating the eye of an observer as projected by a video camera.

The method for detecting pupil diameter is next described. The eye of an observer is first photographed by video camera 108. FIG. 2 shows the appearance of a photographed eye. An image of the pupil is extracted from the image of the photographed eye, and pupil diameter is calculated, with consideration given to the magnification factor involved in photography. In this instance, as illustrated in FIG. 2, pupil diameter is calculated bidirectionally (D1, D2), and the average value thereof is taken as pupil diameter. This method affords precise detection of pupil diameter.

The number of calculated pupil diameters is not limited to 2; just 1, or 3 or more may be calculated.

A line sensor or the like may be used rather than video camera 108. Even if luminance regulator 109 is controlled according to pupil diameter, luminance regulator 109 may also be controlled on the basis of pupil area by detecting pupil area (the region "S" in FIG. 2).

If video camera 108 is used, pupil position as well as pupil diameter can be detected. Consequently, if position data pertaining to a detected pupil is used, the position of the display device with respect to observer eye 101 can be adjusted automatically. Even if the line of sight has moved, the relevant movement data can be provided to image generator 110 as feedback, affording highly precise control.

Figure 3:
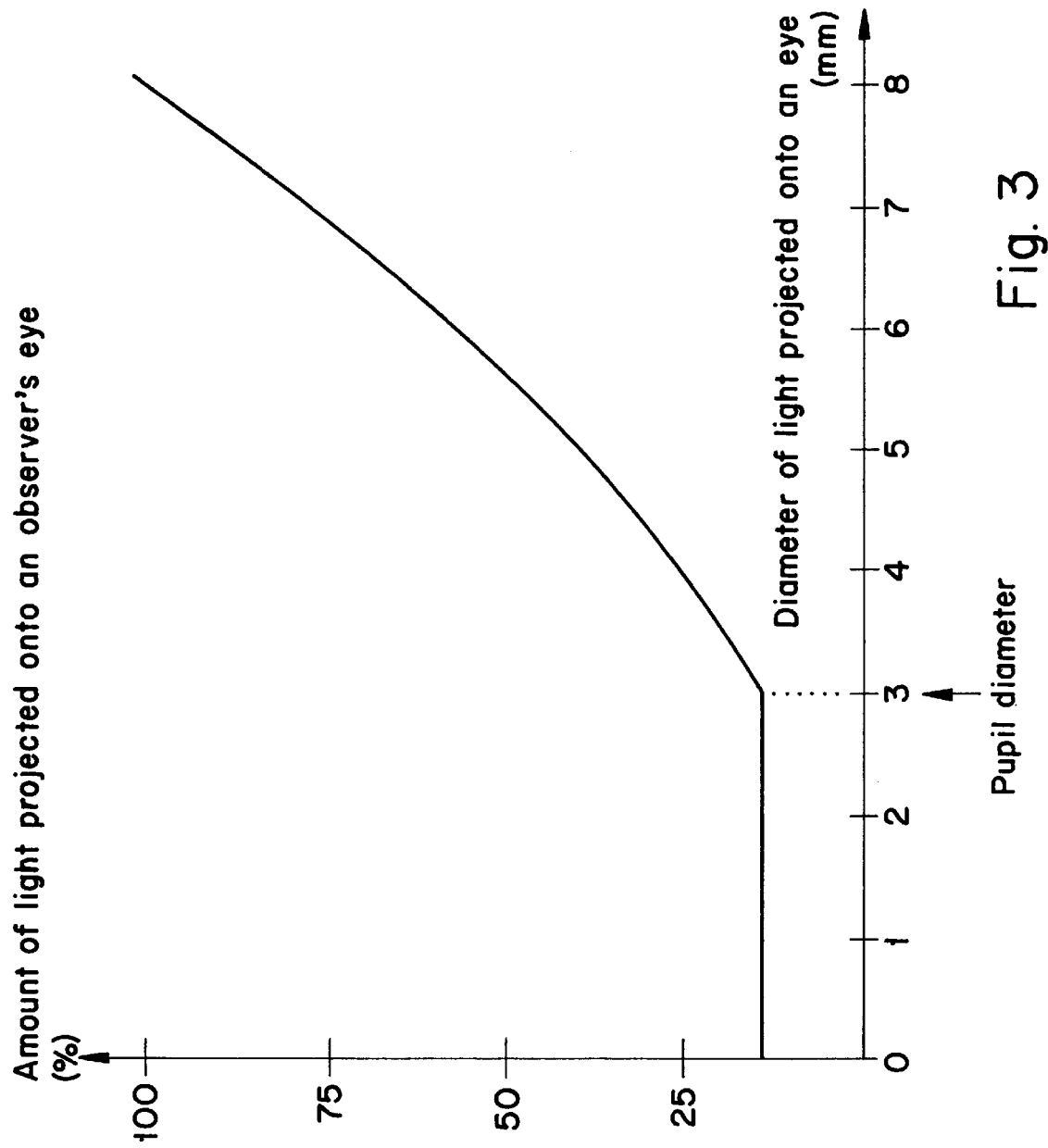
FIG. 3 is a drawing illustrating the relationship between the pupil diameter of an observer and the amount of light incident on an eye as regulated by a luminance regulator.

The method by which luminance regulator 109 controls the amount of light incident at observer eye 101 is next described. FIG. 3 is a graph illustrating the relationship between the pupil diameter of observer eye 101 and the amount of incident light. The graph illustrates the detected pupil diameter of an observer, as shown on the horizontal axis, relative to the amount of light incident at an eye when a unitary image is displayed, as shown on the vertical axis. FIG. 3 illustrates an instance in which the beam diameter of the incident light is 3 mm, but there is no need to restrict or fix this value. The method described hereinafter for controlling the amount of light when the incident light beam diameter is fixed at 3 mm is applicable as a method for controlling the quantity of light when the incident light beam diameter is made a value other than 3 mm, and a description of the latter is therefore omitted.

Under normal circumstances the human pupil is a circle with a diameter varying from roughly 2 to 8 mm. When a given unitary image is displayed, the pupil diameter of the observer is taken as 8 mm, and the amount of light incident on the eye at such time is taken as 100%. If the observer perceives the image as too bright and pupil diameter contracts to 4 mm, pupil area will be one-fourth the original size. Luminance regulator 109 provides control such that the amount of light incident at the eye is reduced to 25% of the original value. In other words, as shown in FIG. 3, luminance regulator 109 controls the quantity of incident light to be nearly proportional to the square of pupil diameter. Such control allows a luminance control function equivalent to actual pupil diameter changes to be offered in a display device.

If the pupil contracts and becomes smaller than the incident light beam diameter of 3 mm, the iris of the observer is able to control the amount of light reaching the retina, and the amount of light incident at observer eye 101 need not be controlled by the device. Thus, when pupil diameter in the present preferred embodiment is less than 3 mm, as shown in FIG. 3, luminance regulator 109 controls the amount of incident light to be 25% of a constant value.

In the present preferred embodiment, the amount of incident light is controlled to be nearly proportional to the square of the pupil diameter of observer eye 101. Control may also be exercised such that the slope of the curved portion of the graph (FIG. 3) is larger or smaller. When control is proportional to the square (as in FIG. 3), the image most closely resembles a natural view to the observer. When the slope is controlled so as to be larger, a flat image results, and when the slope is conversely controlled so as to be smaller, an exaggerated image results.

When an observer views moving images photographed by a camera or moving images produced by computer graphics, the brightness of the displayed images themselves changes continually. In such an instance too, the structure provides that while an observer views an image, pupil diameter is detected continually, and luminance regulator 109 controls the amount of light incident at observer eye 101 according to detection results from video camera 108 as above, without regard to an image signal.

Second Embodiment

Figure 4:
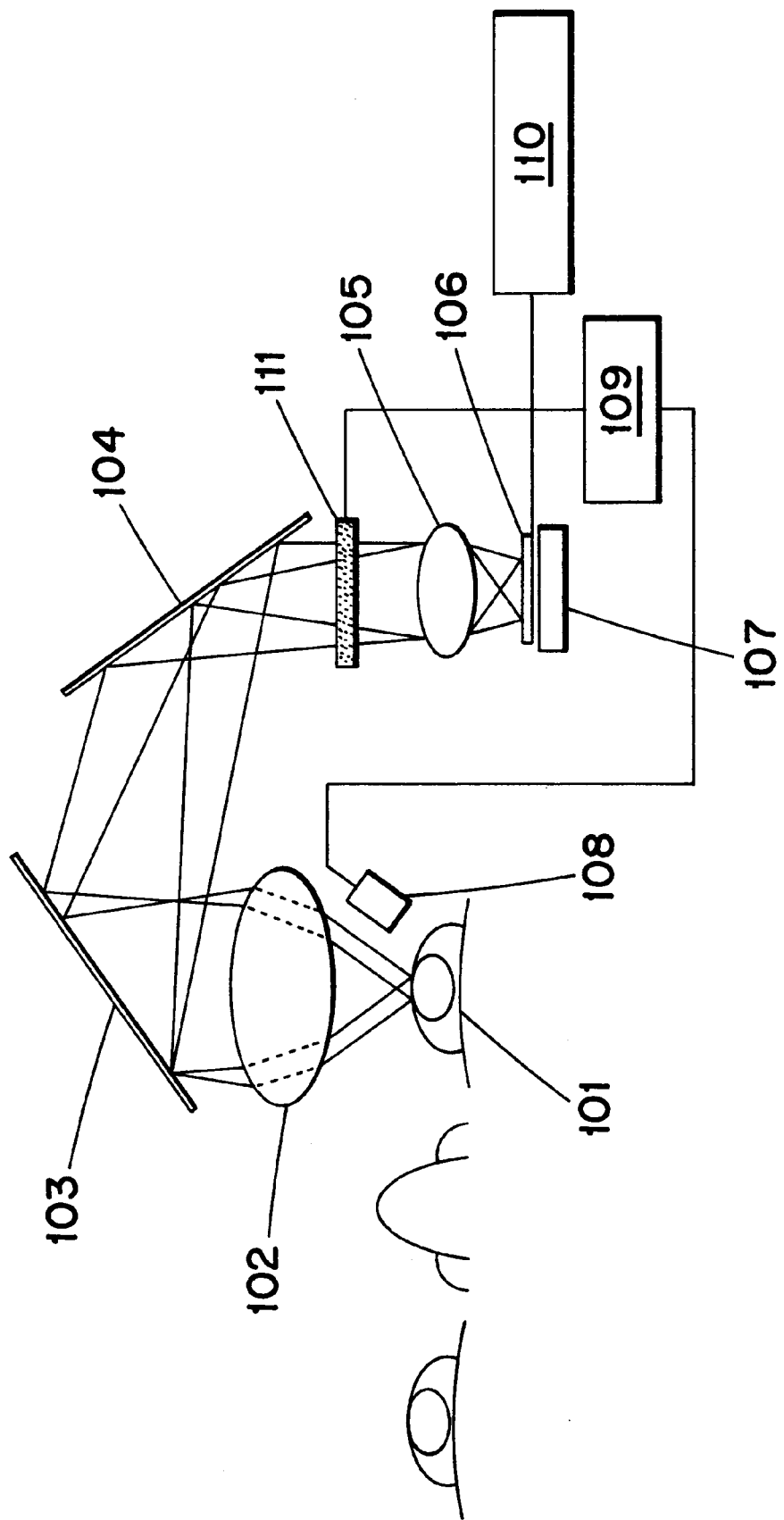
FIG. 4 is a conceptual schematic drawing of a head-mounted display pertaining to a second preferred embodiment.

FIG. 4 is a conceptual schematic drawing of a head-mounted display pertaining to a second preferred embodiment. The head-mounted display pertaining to the present preferred embodiment is structured such that luminance regulator 109 regulates the amount of light incident at observer eye 101 by controlling liquid crystal shutter 111 provided in the light path, rather than controlling the luminance of backlight 107 as in the structure of the first preferred embodiment. The fact that luminance regulator 109 exercises control based on detection results from video camera 108 is the same as in the first preferred embodiment. A similar effect is achieved when liquid crystal shutter 111 is inserted at any location in the light path. The structure of the embodiment and method for control is otherwise the same as in the first preferred embodiment, and a description is therefore omitted. Another element which variably controls the amount of light transmitted may also be used rather than liquid crystal shutter 111.

Third Embodiment

Figure 5:
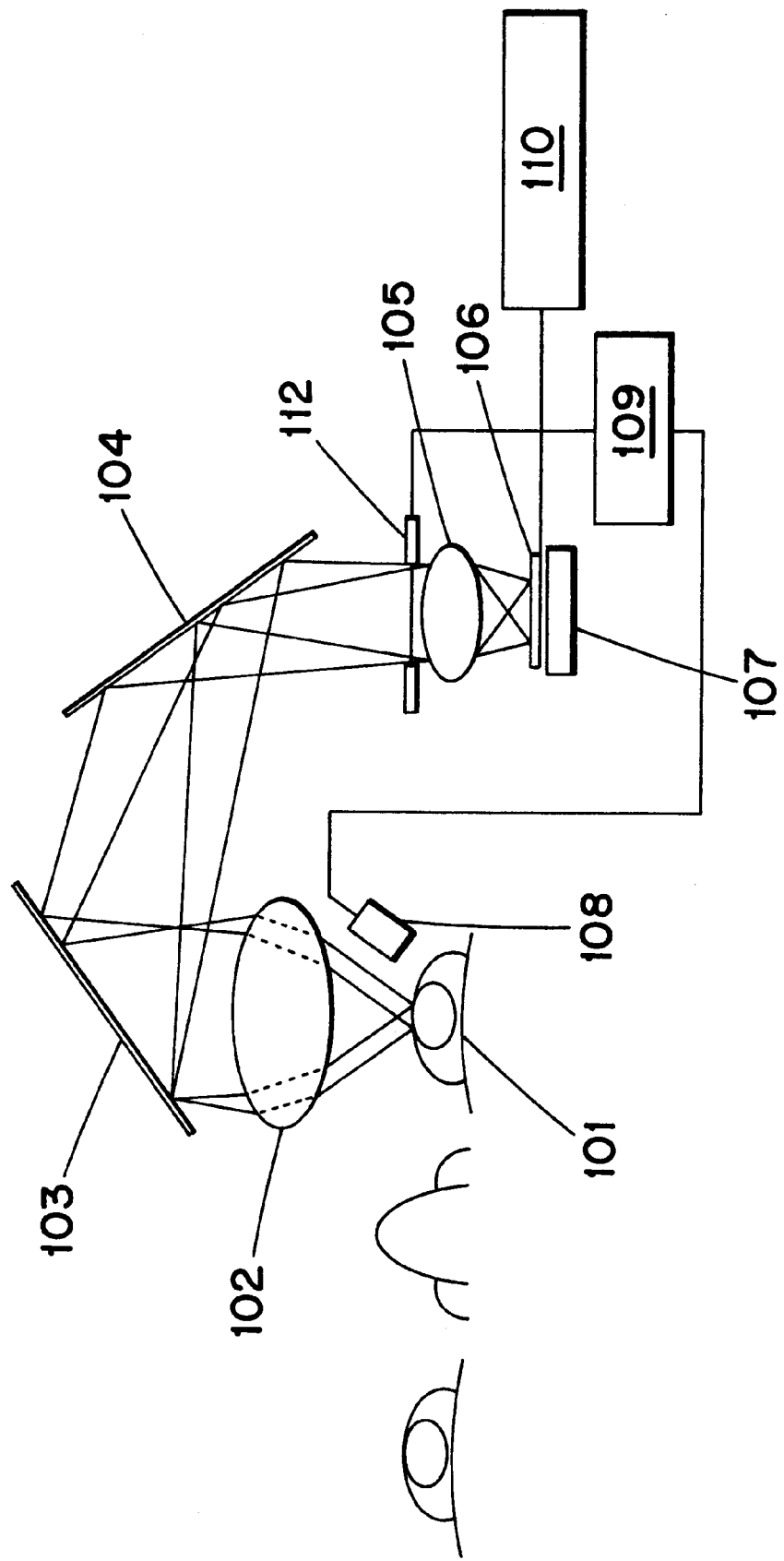
FIG. 5 is a conceptual schematic drawing of a head-mounted display pertaining to a third preferred embodiment.

FIG. 5 is a conceptual schematic drawing of a head-mounted display pertaining to a third preferred embodiment. The head-mounted display pertaining to the present preferred embodiment is structured such that luminance regulator 109 regulates the amount of light incident at observer eye 101 by controlling diaphragm mechanism 112 provided at a near conjugate position to the pupil or at a position near relay optical system 105 and thereby changing the diameter of the incident light beam, rather than controlling the luminance of backlight 107 as in the structure of the first preferred embodiment. The fact that luminance regulator 109 exercises control based on detection results from video camera 108 is the same as in the first preferred embodiment. The structure of the embodiment and method for control is otherwise the same as in the first preferred embodiment, and a description is therefore omitted.

Fourth Embodiment

Figure 6:
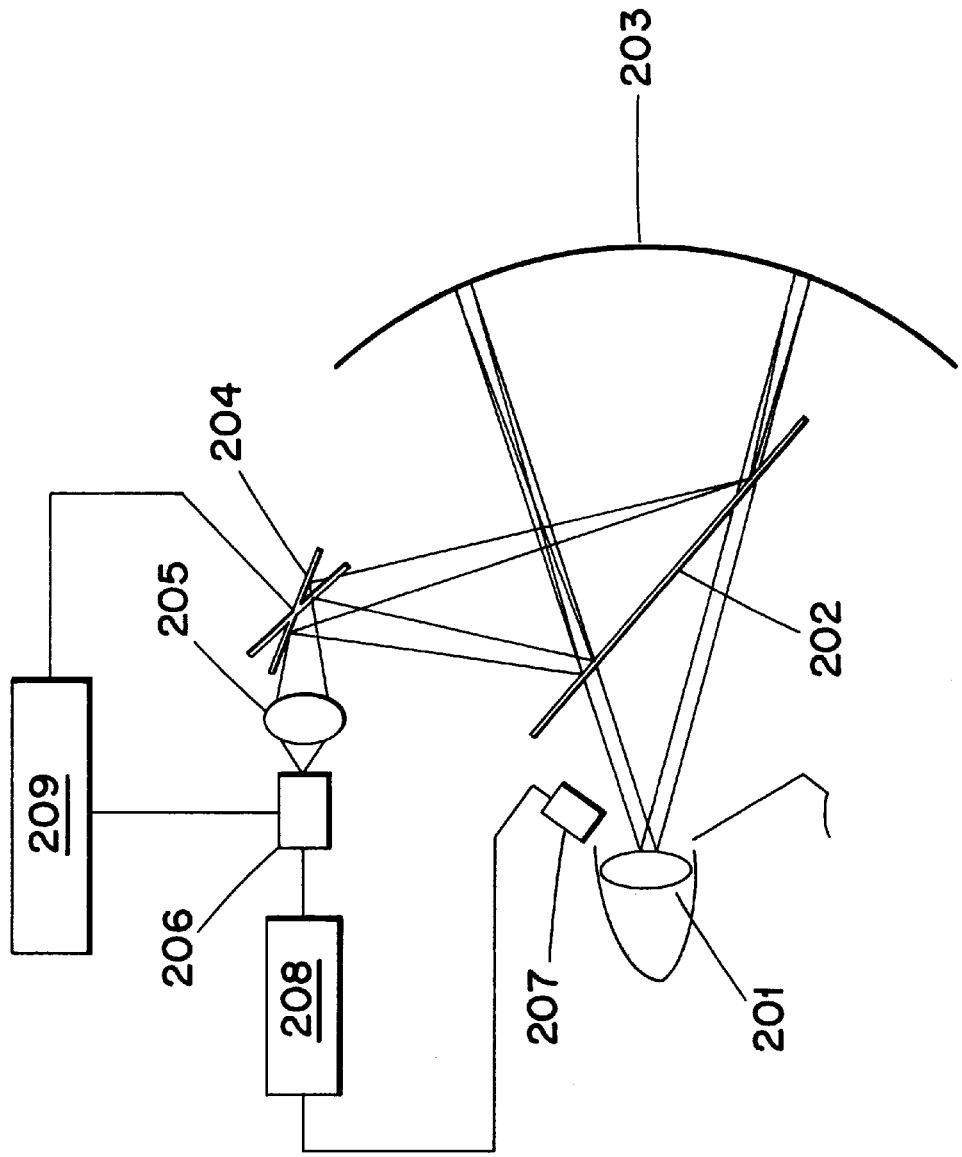
FIG. 6 is a conceptual schematic drawing of a head-mounted display pertaining to a fourth preferred embodiment.

FIG. 6 is a conceptual schematic drawing of a head-mounted display pertaining to a fourth preferred embodiment. The display means of the head-mounted display in the present preferred embodiment comprises laser light source 206 and two-dimensional scanner 204. The movement of a light beam and each structural element are next described.

A light beam emitted from laser light source 206, which is modulated by an image signal from image generator 209, is converged by condenser lens 205 and provided to two-dimensional scanner 204. Two-dimensional scanner 204 is controlled by a control signal from image generator 209 and scans an incident light beam two-dimensionally to form an intermediate image. The intermediate image passes through half-mirror 202 and is viewed as a virtual image by an observer by means of concave lens 203 which has a center of curvature in the vicinity of the eye.

Via concave lens 203, two-dimensional scanner 204 is disposed at a near conjugate position to the pupil of an observer. Thus, the smaller the incident light beam at observer eye 201 is made, the more lightweight and compact two-dimensional scanner 204 can be made. Making two-dimensional scanner 204 lightweight and compact allows scanning at a higher speed, which allows the number of scans in a single image to be increased and also allows more detailed image display.

Numbered element 207 is a pupil diameter detector which makes use of a video camera. Based on the detection results of pupil diameter detector 207, luminance regulator 208 controls the intensity of a laser light source. This control regulates the amount of light incident at observer eye 201. The detection method of pupil diameter detector 207 and the method for control over luminance regulation by luminance regulator 208 are essentially the same as in the first preferred embodiment, and a description is therefore omitted.

It is of course true that a similar effect is obtained when an LED or other point light source is used rather than laser light source 206 in the foregoing structure.

Fifth Embodiment

Figure 7:
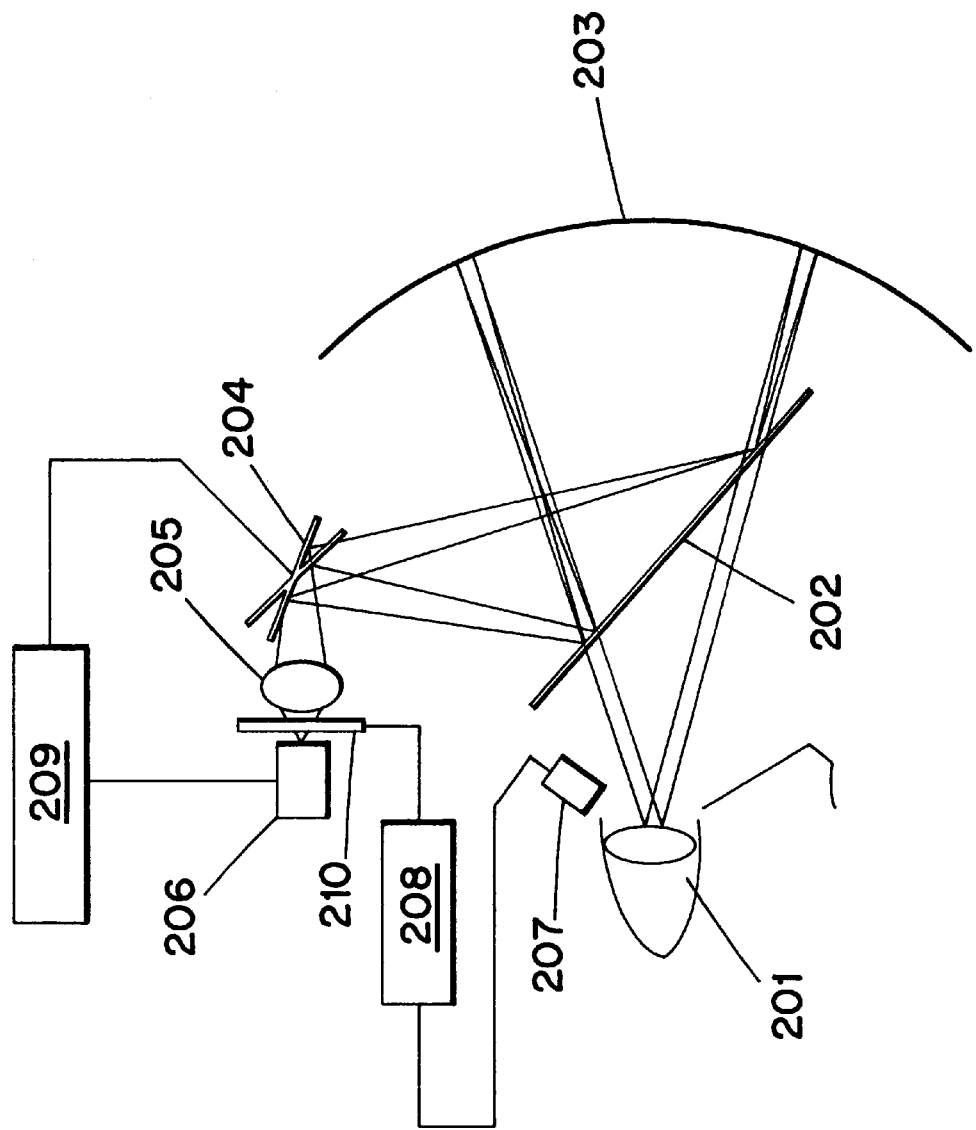
FIG. 7 is a conceptual schematic drawing of a head-mounted display pertaining to a fifth preferred embodiment.

FIG. 7 is a conceptual schematic drawing of a head-mounted display pertaining to a fifth preferred embodiment. The head-mounted display pertaining to the present preferred embodiment is structured such that luminance regulator 208 regulates the amount of light incident at observer eye 201 by controlling laser light modulator 210 comprising an ultrasonic optical element provided in the light path, rather than regulating the amount of light incident at observer eye 201 by controlling the intensity of laser light source 206 as in the fourth preferred embodiment. The structure of the embodiment is otherwise the same as in the fourth preferred embodiment, and a description is therefore omitted.

Sixth Embodiment

Figure 8:
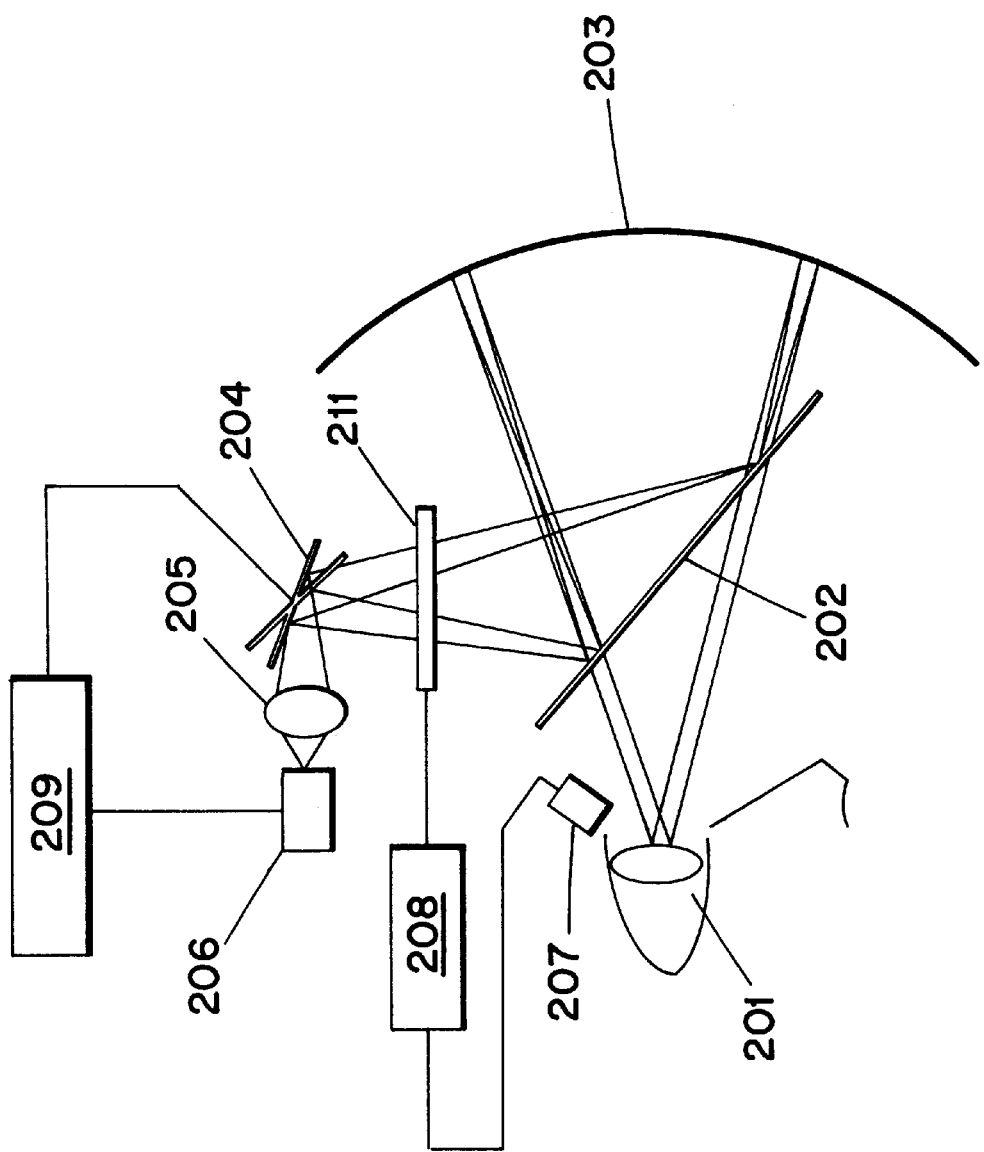
FIG. 8 is a conceptual schematic drawing of a head-mounted display pertaining to a sixth preferred embodiment.

FIG. 8 is a conceptual schematic drawing of a head-mounted display pertaining to a sixth preferred embodiment. The head-mounted display pertaining to the present preferred embodiment is structured such that luminance regulator 208 regulates the amount of light incident at observer eye 201 by controlling liquid crystal shutter 211 provided in the light path, rather than regulating the amount of light incident at observer eye 201 by controlling the intensity of laser light source 206 as in the fourth preferred embodiment. A similar effect is achieved when liquid crystal shutter 211 is inserted at any location in the light path. The structure of the embodiment is otherwise the same as in the fourth preferred embodiment, and a description is therefore omitted. Another element which variably controls the amount of light transmitted may also be used rather than liquid crystal shutter 211.

As described above, the present preferred embodiments function adequately to adjust luminance by changing pupil diameter even when the pupil diameter of an observer is larger than an incident light beam, and the present preferred embodiments thereby offer an environment for enjoying a natural image which is suited to dynamic changes in image signal brightness. An observer is also offered an environment for enjoying a natural image. Safety for the visual function and nerve function of an observer is also assured.

Problems arising when an incident light beam is made fine are also resolved as described above, such that making an incident light beam fine affords a lightweight and compact device.

Although the present invention has been fully described by way of examples with reference to the accompanying drawings, it is to be noted that various changes and modifications will be apparent to those skilled in the art. Therefore, unless such changes and modifications depart from the scope of the present invention, they should be construed as being included therein.

What is claimed is:

1. A display device comprising:
   projection means which projects an image onto an eye of an observer as a virtual image;
   detection means which detects a pupil size of the observer; and
   regulation means which regulates an amount of light presented to the eye according to an pupil size detected by the detection means.

2. A display device of claim 1, wherein said pupil size is represented by a diameter.

3. A display device of claim 2, wherein said regulation means does not regulate the amount of light presented to the eye when the detected pupil diameter is smaller than a diameter of the light.

4. A display device of claim 2, wherein said regulation means regulates the amount of light presented to the eye so that the amount of light is proportional to the square of the pupil diameter.

5. A display device of claim 1, wherein said projection means comprises:
   a light source which emits light based on an image signal;
   scanning means which scans the light in at least two direction; and
   an eyepiece optical system which projects the scanned light onto an eye of an observer as a virtual image.

6. A display device of claim 5, wherein said light source emits a laser beam.

7. A display device of claim 1, wherein said regulation means comprises a liquid crystal shutter.

8. A display device of claim 1, wherein said regulation means comprises a diaphragm mechanism.

9. A display device comprising:
   a light source which emits light based on an image signal;
   scanning means which scans the light emitted from the light source;
   an eyepiece optical system which projects the scanned light onto an eye of an observer as a virtual image;
   detection means which detects a pupil size of the observer; and
   regulation means which regulates a quantity of light projected onto the eye of the observer based on the detected pupil size.

10. A display device of claim 9, wherein said regulation means does not regulate the amount of light presented to the eye when the detected pupil size is smaller than a size of the light.

11. A display device of claim 9, wherein said light source emits a laser beam.

12. A display device of claim 9, wherein said pupil size is represented by a diameter, and said regulation means regulates the amount of light presented to the eye so that the amount of light is proportional to the square of the pupil diameter.

13. A display device of claim 9, wherein said regulation means comprises a liquid crystal shutter.

14. A display device of claim 9, wherein said regulation means comprises a diaphragm mechanism.

15. A display method comprising the steps of:
   projecting an image onto an eye of an observer as a virtual image;
   detecting a pupil size of the eye; and
   regulating a quantity of light projected onto the eye of the observer based on the detected pupil size.

16. A display method comprising the steps of:
   emitting a light based on an image signal;
   scanning the emitted light;
   projecting the scanned light onto an eye of an observer as a virtual image;
   detecting a pupil size of the eye; and
   regulating a quantity of light projected onto the eye of the observer based on the detected pupil size.

17. A display method of claim 16, wherein said light is a laser beam.

18. A display method comprising the steps of:
   displaying an image based on an image signal;
   projecting the image onto an eye of an observer as a virtual image; and
   regulating brightness of the image based on the image signal.

* * * * *